United States Patent
Joergensen

(10) Patent No.: US 11,260,108 B2
(45) Date of Patent: Mar. 1, 2022

(54) MIC-1 AND GLP-1 FOR USE IN THE TREATMENT OF OBESITY

(71) Applicant: Novo Nordisk A/S, Bagsvaerd (DK)

(72) Inventor: Sebastian Beck Joergensen, Virum (DK)

(73) Assignee: Novo Nordisk A/S, Bagsvaerd (DK)

( * ) Notice: Subject to any disclaimer, the term of this patent is extended or adjusted under 35 U.S.C. 154(b) by 59 days.

(21) Appl. No.: 16/645,828

(22) PCT Filed: Sep. 10, 2018

(86) PCT No.: PCT/EP2018/074263
§ 371 (c)(1),
(2) Date: Mar. 10, 2020

(87) PCT Pub. No.: WO2019/048660
PCT Pub. Date: Mar. 14, 2019

(65) Prior Publication Data
US 2020/0197491 A1    Jun. 25, 2020

(30) Foreign Application Priority Data
Sep. 10, 2017   (EP) .................................... 17190270

(51) Int. Cl.
| | |
|---|---|
| *A61K 38/19* | (2006.01) |
| *A61P 3/02* | (2006.01) |
| *A61K 9/00* | (2006.01) |
| *A61K 38/26* | (2006.01) |
| *A61P 3/04* | (2006.01) |
| *A61K 47/64* | (2017.01) |

(52) U.S. Cl.
CPC ............ *A61K 38/19* (2013.01); *A61K 9/0019* (2013.01); *A61K 9/0053* (2013.01); *A61K 38/26* (2013.01); *A61K 47/643* (2017.08); *A61P 3/02* (2018.01); *A61P 3/04* (2018.01)

(58) Field of Classification Search
None
See application file for complete search history.

(56) References Cited

U.S. PATENT DOCUMENTS
2015/0307575 A1   10/2015  Xiong
2016/0120999 A1   5/2016   Shen et al.

FOREIGN PATENT DOCUMENTS

| WO | 2005099746 A1 | 10/2005 |
|---|---|---|
| WO | 2006/097537 A2 | 9/2006 |
| WO | 2013148117 A1 | 10/2013 |
| WO | 2014120619 A2 | 8/2014 |
| WO | 2015197446 A1 | 12/2015 |
| WO | 2015198199 A1 | 12/2015 |
| WO | 2016018931 | 2/2016 |

OTHER PUBLICATIONS

Mehta et al. ("Liraglutide for weight management: a critical review of the evidence," Obes Sci Pract. Mar. 2017; 3(1): 3-14) (Year: 2017).*
Blundell et al. ("Effects of once-weekly semaglutide on appetite, energy intake, control of eating, food preference and body weight in subjects with obesity," Diabetes Obes Metab. 2017;19:1242-1251) (Year: 2017).*
Bauskin, A.,R., "The Propeptide of Macrophage Inhibitory Cytokine (MIC-1), a TGF-ß Superfamily Member, Acts as a Quality Control Determinant for Correctly Folded MIC-1," The EMBO Journal, 2000, vol. 19, No. 10, pp. 2212-2220.
Bootcov et al., "MIC-1, a Novel Macrophage Inhibitory Cytokine, is a Divergent Member of the TGF-ß Superfamily," Proc. Natl. Acad. Sci. USA, Oct. 1997, vol. 94, pp. 11514-11519.
Johnen et al, "Tumor-Induced Anorexia and Weight Loss are Mediated by the TGF-ß Superfamily Cytokine MIC-1," Nature Medicine, Nov. 2007, vol. 13, No. 11, pp. 1333-1340.
Knudsen LB, "Long-Acting Glucagon-Like Peptide-1 Receptor Agonists Have Direct Access to and Effects on Pro-Opiomelanocortin/ Cocaine- and Amphetamine-Stimulated Transcript Neurons in the Mouse Hypothalamus," Journal of Diabetes Investigation, Apr. 2016, vol. 7, No. 51, pp. 56-63.
Macia et al, "Macrophage Inhibitory Cytokine 1 (MIC-1/GDF15) Decreases Food Intake, Body Weight and Improves Glucose Tolerance in Mice on Normal & Obesogenic Data," PLoS One, Apr. 2012, vol. 7, No. 4, e34868.

* cited by examiner

*Primary Examiner* — Christina Bradley
(74) *Attorney, Agent, or Firm* — Leon Lum

(57) ABSTRACT

The invention relates to MIC-1 compounds for use in the prevention and/or treatment of obesity, wherein the MIC-1 compounds is administered simultaneously, separately or sequentially with a GLP-1 compound.

18 Claims, No Drawings
Specification includes a Sequence Listing.

SEQUENCE LISTING

```
<160> NUMBER OF SEQ ID NOS: 2

<210> SEQ ID NO 1
<211> LENGTH: 112
<212> TYPE: PRT
<213> ORGANISM: Homo sapiens

<400> SEQUENCE: 1

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 2
<211> LENGTH: 31
<212> TYPE: PRT
<213> ORGANISM: Homo sapiens
```

```
<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30
```

MIC-1 AND GLP-1 FOR USE IN THE TREATMENT OF OBESITY

CROSS-REFERENCE TO RELATED APPLICATIONS

This application is a 35 U.S.C. § 371 National Stage application of International Application PCT/EP2018/074263 (WO/2019/048660), filed Sep. 10, 2018, which claims priority to European Patent Application 17190270.3, filed Sep. 10, 2017, the contents of all above-named applications are incorporated herein by reference.

TECHNICAL FIELD OF INVENTION

The present invention relates to MIC-1 compounds and their use in the treatment of obesity.

INCORPORATION-BY-REFERENCE OF THE SEQUENCE LISTING

SEQ ID NO:1 is native human MIC-1 (112 amino acid MIC-1 sequence): ARNGDHCPLGPGRCCRLHTVRASLEDLGWADVVVLSPRE-VQVTMCIGACPSQFRAANMHA QIKTSLHRLKPDTVPAPCCVPASYNPMVLIQKTDTGVSLQTYDDLLAKDCHCI.

SEQ ID NO:2 is the native human GLP-1(7-37)) sequence: HAEGTFTSDVSSYLEGQAAKEFIAWLVKGRG.

BACKGROUND OF THE INVENTION

Macrophage Inhibitory Cytokine-1 (MIC-1) was first described in 1997 (Bootcov et al, Proc. Natl. Acad. Sci. October 1997) based on experiments showing increased expression in activated macrophages. MIC-1 has subsequently been identified by others and given several additional names such as placental transforming growth factor beta (PTGF-β), placental bone morphogenetic protein, growth differentiation factor-15 (GDF15), prostate derived factor (PDF), non-steroidal anti-inflammatory drug-activated gene (NAG-1) and PL74. MIC-1 is a distant member of the TGF-beta super family, a family of peptide hormones involved in cell growth and differentiation. MIC-1 circulates as a cysteine-rich homodimer with a molecular mass of 24.5 kDa. Human wild-type MIC-1 has a short half-life, meaning that treatment with wt-MIC-1 requires daily administration to maintain efficacy.

Accumulating evidence support the therapeutic utility of MIC-1 in metabolic disorders such as obesity. Data from patients with advanced cancer showed that weight loss correlated with circulating levels of MIC-1 (Johnen et al, Nat. Med., November, 2007). Transgenic mice overexpressing MIC-1 gain less weight and body fat both on a normal low fat diet and on a high fat diet (Macia et al, PLoS One, April, 2012). Also, transgenic mice overexpressing MIC-1 fed both on a low and high fat diet, respectively, had improved glucose tolerance compared with wild type animals on a comparable diet.

WO 2005099746 concerns a method of modulating appetite and/or body weight by administering a MIC-1 modulating agent.

SUMMARY OF THE INVENTION

The present invention relates to MIC-1 compounds and their use in the prevention and/or treatment of obesity, wherein the MIC-1 compound is administered simultaneously, separately or sequentially with a GLP-1 compound.

In an aspect, the present invention also relates to Methods of prevention and/or treatment of obesity, wherein a MIC-1 compound is administered simultaneously, separately or sequentially with a GLP-1 compound.

DETAILED DESCRIPTION OF THE INVENTION

The present invention relates to MIC-1 compounds and their use in the prevention and/or treatment of obesity, wherein the MIC-1 compound is administered simultaneously, separately or sequentially with a GLP-1 compound.

MIC-1 Compounds

The term "MIC-1" as used herein means Macrophage Inhibitory Cytokine-1 (MIC-1), also known as Growth Differentiation Factor 15 (GDF-15), placental bone morphogenetic protein (PLAB) and nonsteroidal anti-inflammatory drug-activated gene (NAG-1). MIC-1 is synthesized as a 62 kDa intracellular homodimer precursor protein which subsequently is cleaved by a furin-like protease into a 24.5 kDa homodimer. The sequence of the full length wild type human MIC-1 is available from the UNIPROT database with accession no. Q99988. The 308 amino acid precursor sequence includes a signal peptide (amino acids 1-29), a propeptide (amino acids 30-196) and a MIC-1 monomer sequence (amino acids 197-308). The 112 amino acid MIC-1 monomer sequence is included herein as SEQ ID NO:1. MIC-1 monomer contains nine cysteine residues which give rise to the formation of 4 intrachain disulphide bonds and one interchain disulphide bond to create a covalently linked 24.5 kDa homodimer. A naturally occurring mutation corresponding to H6D in the MIC-1 monomer sequence (SEQ ID NO:1) has been described.

The term "MIC-1 compound", as used herein, refers to MIC-1 or a MIC-1 polypeptide; or a derivative, a conjugate or a fusion protein of MIC-1 or a MIC-1 polypeptide.

The MIC-1 compound is typically in the form of a homodimer.

The term "MIC-1 polypeptide" as used herein refer to the human MIC-1 monomer sequence of SEQ ID NO:1 or an analogue thereof. Numerical references to particular MIC-1 residues, if not stated otherwise, refer to the 112 amino acid monomer sequence (i.e., residue 1 is Alanine (A1), and residue 112 is Isoleucine (I112).

In an embodiment of the invention, the MIC-1 compound is a MIC-1 polypeptide.

The term "MIC-1 analogue" as used herein refers to a MIC-1 polypeptide in which a number of amino acid changes have been made to the human MIC-1 sequence of SEQ ID NO:1. These amino acid changes may be substitutions, extensions, insertions, and/or deletions as compared to SEQ ID NO: 1. In other words, a MIC-1 analogue is a MIC-1 polypeptide in which a number of amino acid residues have been changed when compared to human MIC-1 (SEQ ID NO: 1).

In an embodiment of the invention, the MIC-1 compound is a MIC-1 analogue.

In one aspect, the MIC-1 analogue is a functional variant of the MIC-1 of SEQ ID NO:1. In one aspect of the invention, the MIC-1 analogues display at least 85%, 90% or 95% sequence identity to MIC-1 of SEQ ID NO:1. As an example of a method for determination of the sequence identity between two analogues the two peptides H6D MIC-1 and MIC-1 of SEQ ID NO:1 are aligned. The sequence identity of the H6D MIC-1 analogue relative to MIC-1 of SEQ ID NO:1 is given by the number of aligned identical residues minus the number of different residues divided by the total number of residues in MIC-1 of SEQ ID NO:1. Accordingly, in said example the sequence identity in percentage is (112-1)/112×100.

In another aspect of the invention, the MIC-1 analogues comprise less than 15, 10 or 5, amino acid modifications (substitutions, deletions, additions (including insertions) and any combination thereof) relative to human MIC-1 of SEQ ID NO:1. The term "amino acid modification" used throughout this application is used in the meaning of a modification to an amino acid as compared to monomer MIC-1 (SEQ ID NO:1). This modification can be the result of a deletion of an amino acid, addition of an amino acid, substitution of one amino acid with another or a substituent covalently attached to an amino acid of the peptide.

Substitutions: In one aspect amino acids may be substituted by conservative substitution. The term "conservative substitution" as used herein denotes that one or more amino acids are replaced by another, biologically similar residue. Examples include substitution of amino acid residues with similar characteristics, e.g. small amino acids, acidic amino acids, polar amino acids, basic amino acids, hydrophobic amino acids and aromatic amino acids. In one aspect amino acids may be substituted by non-conservative substitution. The term "non-conservative substitution" as used herein denotes that one or more amino acids are replaced by another amino acid having different characteristics. Examples include substitution of a basic amino acid residue with an acidic amino acid residue, substitution of a polar amino acid residue with an aromatic amino acid residue, etc. In one aspect, the non-conservative substitution is substitution of a coded amino acid to another coded amino acid having different characteristics. In one aspect, the MIC-1 analogues may comprise substitutions of one or more unnatural and/or non-amino acids, e.g., amino acid mimetics, into the sequence of MIC-1.

Deletions and Truncations: In one aspect, the MIC-1 analogues of the invention may have one or more amino acid residues deleted from the amino acid sequence of MIC-1 (SEQ ID NO:1), alone or in combination with one or more insertions or substitutions.

Insertions: In one aspect, the MIC-1 analogues of the invention have one or more amino acid residues inserted into the amino acid sequence of human MIC-1, alone or in combination with one or more deletions and/or substitutions. In one aspect, the MIC-1 analogues of the invention include insertions of one or more unnatural amino acids and/or non-amino acids into the sequence of MIC-1.

Extensions: In one aspect, the MIC-1 analogues of the invention may comprise one or two amino acid extensions compared to the amino acid sequence of MIC-1 (SEQ ID NO:1), alone or in combination with one or more insertions, deletions or substitutions.

In an embodiment of the invention, the MIC-1 compound has an N-terminal amino acid extension.

The term "MIC-1 derivative" as used herein means a chemically modified MIC-1 peptide, in which one or more substituents have been covalently attached to the peptide. The substituent may also be referred to as a side chain.

In an embodiment of the invention, the side chain is a fatty acid side chain.

The term "MIC-1 conjugate" as used herein means a chemically conjugated MIC-1 peptide, in which one or more conjugtor(s) have been covalently attached to the peptide.

The term "Fusion protein" as used herein means a hybrid protein expressed by a nucleic acid molecule comprising nucleotide sequences of at least two protein genes. Fusion proteins are often used for improving recombinant expression or stability of therapeutic proteins as well as for improved recovery and purification of such proteins from cell cultures and the like. Fusion proteins may comprise artificial sequences, e.g. a linker sequence.

"MIC-1 fusion protein" as used herein is also intended to mean covalent joining of MIC-1 with at least one other protein and/or peptide, such as albumin or a Fc region of an antibody. In one aspect, the fusion protein of the invention comprises MIC-1 fused with human serum albumin (MIC-1-HSA).

In an embodiment of the invention, the MIC-1 compound is a MIC-1-HSA as disclosed in WO 2015/197446, Example 1.

The MIC-1 compounds of the invention have MIC-1 activity. This term refers to the ability to bind to the MIC-1 (GFRAL) receptor and initiate a signal transduction (as described in WO/2017/121865)

Non-limiting examples of MIC-1 compounds are disclosed in WO 2017/109706, WO 2013/148117, WO 2014/120619, WO 2012/138919, WO 2013/113008, WO 2015/017710.

MIC-1 Receptor Agonists

A receptor agonist may be defined as a compound that binds to a receptor and elicits a response typical of the natural ligand. A full agonist may be defined as one that elicits a response of the same magnitude as the natural ligand (see e.g. "Principles of Biochemistry", AL Lehninger, DL Nelson, MM Cox, Second Edition, Worth Publishers, 1993, page 763).

Thus, for example, a "MIC-1 receptor agonist" may be defined as a compound which is capable of binding to the MIC-1 receptor and capable of activating it. And a "full" MIC-1 receptor agonist may be defined as a MIC-1 receptor agonist which is capable of eliciting a magnitude of MIC-1 receptor response that is similar to native MIC-1.

In an aspect of the present invention the MIC-1 receptor agonist is administered simultaneously, separately or sequentially with a GLP-1 compound.

GLP-1 Compounds

The term "GLP-1 compound" as used herein refers to a GLP-1 peptide or a derivative, conjugate or fusion protein thereof.

The term "GLP-1 peptide" as used herein refers to the human Glucagon-Like Peptide-1 (GLP-1(7-37)), the sequence of which is included in the sequence listing as SEQ ID NO: 2, or an analogue thereof. The peptide having the sequence of SEQ ID NO: 2 may also be designated "native" GLP-1.

In an embodiment of the invention, the GLP-1 compound is a GLP-1 peptide.

The term "GLP-1 analogue" as used herein refers to a GLP-1 peptide in which a number of amino acid changes have been made to native GLP-1(7-37) (SEQ ID NO: 2). These amino acid changes may be substitutions, extensions, insertions, and/or deletions as compared to native GLP-1(7-37) (SEQ ID NO: 2).

In an embodiment of the invention, the GLP-1 compound is a GLP-1 analogue.

In an embodiment, the GLP-1 analogue is a functional variant of the GLP-1 of SEQ ID NO:2. In an embodiment of the invention, the GLP-1 analogues display at least 85%, 90% or 95% sequence identity to GLP-1 of SEQ ID NO:2. In an embodiment of the invention, the GLP-1 analogues comprise less than 7, 5 or 3, amino acid modifications (substitutions, deletions, additions (including insertions) and any combination thereof) relative to human GLP-1 of SEQ ID NO:2.

Substitutions: In one aspect, the GLP-1 analogues of the invention may comprise substitutions of one or more amino acids of the amino acid sequence of GLP-1 (SEQ ID NO:2), alone or in combination with one or more insertions, extensions or deletions. In one aspect, the MIC-1 analogues may comprise substitutions of one or more unnatural and/or non-amino acids, e.g., amino acid mimetics, into the sequence of GLP-1.

Extensions: In one aspect, the GLP-1 analogues of the invention may comprise one or two amino acid extensions compared to the amino acid sequence of GLP-1 (SEQ ID NO:2), alone or in combination with one or more insertions, deletions or substitutions.

Insertions: In one aspect, the GLP-1 analogues of the invention may have one or more amino acid residues inserted into the amino acid sequence of GLP-1 (SEQ ID NO:2), alone or in combination with one or more deletions, extensions or substitutions.

Deletions and Truncations: In one aspect, the GLP-1 analogues of the invention may have one or more amino acid residues deleted from the amino acid sequence of GLP-1 (SEQ ID NO:2), alone or in combination with one or more insertions, extensions or substitutions.

The term "GLP-1 derivative" as used herein means a chemically modified GLP-1 peptide, in which one or more substituents have been covalently attached to the peptide. The substituent may also be referred to as a side chain.

The term "GLP-1 conjugate" as used herein means a chemically conjugated GLP-1 peptide, in which one or more conjugtor(s) have been covalently attached to the peptide.

The term "GLP-1 fusion proteins" as used herein is also intended to mean covalent joining of GLP-1 with at least one other protein and/or peptide, such as albumin or a Fc region of an antibody.

The GLP-1 compounds of the invention have GLP-1 activity. This term refers to the ability to bind to the GLP-1 receptor and initiate a signal transduction pathway resulting in insulinotropic action or other physiological effects as is known in the art.

Non-limiting examples of GLP-1 compounds are disclosed in WO 98/08871, WO 98/08871 and U.S. Pat. No. 5,424,286.

In an embodiment of the invention, the GLP-1 compound is liraglutide. Liraglutide is a mono-acylated GLP-1 derivative for once daily administration which is marketed as of 2009 by Novo Nordisk A/S and is disclosed in WO 98/08871, Example 37.

In an embodiment of the invention, the GLP-1 compound is semaglutide. Semaglutide is a mono-acylated GLP-1 derivative for once weekly administration which is under development by Novo Nordisk A/S and is disclosed in WO 2006/097537, Example 4.

In an embodiment of the invention, the GLP-1 compound is dulaglutide. Dulaglutide is a GLP-1-Fc construct (GLP-1-linker-Fc from IgG4).

In an embodiment of the invention, the GLP-1 compound is exenatide. Exenatide is a synthetic version of exendin-4, a hormone found in the saliva of the Gila monster. It displays biological properties similar to GLP-1. Exenatide is disclosed in U.S. Pat. No. 5,424,286.

In an embodiment of the invention, the GLP-1 compound is lixisenatide. Lixisenatide is based on exendin-4(1-39) modified C-terminally with six Lys residues. Lixisenatide is disclosed in Wikipedia reference is (Drugs, 2009 August; 12(8):503-13)].

In an embodiment of the invention, the GLP-1 compound is albiglutide. Albiglutide is a recombinant human serum albumin (HSA)-GLP-1 hybrid protein. The constituent GLP-1 peptide is an analogue, in which Ala at position 8 has been substituted by Gly. Albiglutide is disclosed in Wikipedia reference is Curr. Opin. Mol. Ther., 2009 October; 11(5):579-88].

GLP-1 Receptor Agonists

A receptor agonist may be defined as a compound that binds to a receptor and elicits a response typical of the natural ligand. A full agonist may be defined as one that elicits a response of the same magnitude as the natural ligand (see e.g. "Principles of Biochemistry", A L Lehninger, D L Nelson, M M Cox, Second Edition, Worth Publishers, 1993, page 763).

Thus, for example, a "GLP-1 receptor agonist" may be defined as a compound which is capable of binding to the GLP-1 receptor and capable of activating it. And a "full" GLP-1 receptor agonist may be defined as a GLP-1 receptor agonist which is capable of eliciting a magnitude of GLP-1 receptor response that is similar to native GLP-1.

In an aspect of the present invention a MIC-1 compound is administered simultaneously, separately or sequentially with a GLP-1 receptor agonist.

Pharmaceutical Indications—Obesity

In one aspect, the present invention relates to the compounds of the invention, for use as medicament in the use for the prevention and/or treatment of eating disorders, such as obesity (an excessive amount of body fat), e.g. by decreasing food intake, reducing body weight, and suppressing appetite.

Generally, all subjects suffering from obesity are also considered to be suffering from overweight. In some embodiments the invention relates to a method for treatment or prevention of obesity. In some embodiments the invention relates to use of the MIC-1 compounds in combination with GLP-1 compounds for treatment or prevention of obesity. In some embodiments the subject suffering from obesity is human, such as an adult human or a paediatric human (including infants, children, and adolescents). Body mass index (BMI) is a measure of body fat based on height and weight. The formula for calculation is BMI=weight in kilograms/height in meters$^2$. A human subject suffering from obesity has a BMI of ≥30; this subject may also be referred to as obese. In some embodiments the human subject suffering from obesity has a BMI of ≥35 or a BMI in the range of ≥30 to <40. In some embodiments the obesity is severe obesity or morbid obesity, wherein the human subject has a BMI of 40.

In some embodiments the invention relates to a method for treatment or prevention of overweight, optionally in the presence of at least one weight-related comorbidity. In some embodiments the invention relates to use of the MIC-1 compounds and GLP-1 compounds of the invention for treatment or prevention of overweight, optionally in the presence of at least one weight-related comorbidity.

In some embodiments the subject suffering from overweight is human, such as an adult human or a paediatric human (including infants, children, and adolescents). In some embodiments a human subject suffering from overweight has a BMI of ≥25, such as a BMI of ≥27. In some embodiments a human subject suffering from overweight has a BMI in the range of 25 to <30 or in the range of 27 to <30. In some embodiments the weight-related comorbidity is selected from the group consisting of hypertension, diabetes (such as type 2 diabetes), dyslipidaemia, high cholesterol, and obstructive sleep apnoea.

In some embodiments the invention relates to a method for reduction of body weight. In some embodiments the invention relates to use of the MIC-1 compounds and GLP-1 compounds of the invention for reduction of body weight. A human to be subjected to reduction of body weight according to the present invention has a BMI of ≥25, such as a BMI of ≥27 or a BMI of ≥30. In some embodiments the human to be subjected to reduction of body weight according to the present invention has a BMI of ≥35 or a BMI of ≥40.

Mode of Administration

The amount of the compounds of this invention to be administered, the determination of how frequently to administer a compound of this invention, and the election of which compound or compounds of this invention to administer, optionally together with another pharmaceutically active agent, is decided in consultation with a practitioner who is familiar with the treatment of obesity and related disorders.

The route of administration may be any route which effectively transports a compound of this invention to the desired or appropriate place in the body, such as parenterally, for example, subcutaneously, intramuscularly or intravenously. Alternatively, a compound of this invention can be administered orally, pulmonary, rectally, transdermally, buccally, sublingually, or nasally.

In one embodiment of the invention the MIC-1 compound and the GLP-1 compound is administered subcutaneously.

In one embodiment of the invention the MIC-1 compound and the GLP-1 compound is administered orally.

In one embodiment of the invention the MIC-1 compound is administered subcutaneously and the GLP-1 compound is administered orally.

In one embodiment of the invention the dosage of the MIC-1 compound is 5-1000 nmol/individual/injection.

In one embodiment of the invention the dosage of the GLP-1 compound is 0.3-5.0 mg/individual/injection.

In one embodiment of the invention the dosage of semaglutide is 0.3-5.0 mg/individual/injection.

In one embodiment of the invention the dosage of liraglutide is 1.2-3.0 mg/individual/injection.

Administered Simultaneously, Separately or Sequentially

By simultaneously, within the meaning of the present invention is meant an administration of the MIC-1 compound and the GLP-1 compound by the same route and at the same time or at substantially the same time.

By separately, within the meaning of the present invention is meant in particular an administration of the MIC-1 compound and the GLP-1 compound at the same time or at substantially the same time by different routes.

By sequentially is meant administration of the MIC-1 compound and the GLP-1 compound at different times, the administration route being identical or different. More particularly by an administration method is meant according to which the whole administration of one of the active ingredients is carried out before administration of the other or others commences. It is thus possible to administer one of the active ingredients over several months before administering the other active ingredient or ingredients. There is no simultaneous treatment in this case. An alternate administration of each active ingredient over several weeks can also be envisaged.

In one embodiment of the invention the MIC-1 compound is administered simultaneously with the GLP-1 compound.

In one embodiment of the invention the MIC-1 compound is administered separately with the GLP-1 compound.

In one embodiment of the invention the MIC-1 compound is administered sequentially with the GLP-1 compound.

In one embodiment of the invention the MIC-1 compound is administered once daily, once weekly or once monthly.

In one embodiment of the invention the GLP-1 compound is administered once daily, once weekly or once monthly.

Pharmaceutical Compositions

Pharmaceutical compositions comprising the compounds of the invention or a pharmaceutically acceptable salt, amide, or ester thereof, and a pharmaceutically acceptable excipient may be prepared as is known in the art.

The term "excipient" broadly refers to any component other than the active therapeutic ingredient(s). The excipient may be an inert substance, an inactive substance, and/or a not medicinally active substance.

The excipient may serve various purposes, e.g. as a carrier, vehicle, diluent, tablet aid, and/or to improve administration, and/or absorption of the active substance.

The formulation of pharmaceutically active ingredients with various excipients is known in the art, see e.g. Remington: The Science and Practice of Pharmacy (e.g. 19th edition (1995), and any later editions).

Unless otherwise indicated in the specification, terms presented in singular form also include the plural situation", e.g. "a" means "one or more".

Particular Embodiments

The invention is further described by the following non-limiting embodiments of the invention:

Embodiment 1: MIC-1 compound for use in the prevention and/or treatment of obesity, wherein the MIC-1 compound is administered simultaneously, separately or sequentially with a GLP-1 compound.

Embodiment 2: MIC-1 compound according to embodiment 1, wherein the MIC-1 compound is a MIC-1 fusion protein.

Embodiment 3: MIC-1 compound according to claim 2, wherein the MIC-1 fusion protein is a MIC-1 fused with human serum albumin (MIC-1-HSA).

Embodiment 4: MIC-1 compound according to embodiment 2, wherein the MIC-1 fusion protein is a MIC-1 fused with Fc region of an antibody (MIC-1-Fc fusion).

Embodiment 5: MIC-1 compound according to embodiment 1, wherein the MIC-1 compound is a MIC-1 derivative and comprises a fatty acid side chain.

Embodiment 6: MIC-1 compound according to embodiments 1 and 5, wherein the MIC-1 compound has a N-terminal amino acid extension and comprise a fatty acid side chain.

Embodiment 7: MIC-1 compound according to embodiment 1, wherein the GLP-1 compound is semaglutide.

Embodiment 8: MIC-1 compound according to embodiment 1, wherein the GLP-1 compound is a liraglutide.

Embodiment 9: MIC-1 compound according to embodiment 3 and 7, wherein the MIC-1 compound is a MIC-1 fused with human serum albumin and the GLP-1 compound is semaglutide.

Embodiment 10: MIC-1 compound according to embodiment 3 and 8, wherein the MIC-1 compound is a MIC-1 fused with human serum albumin and the GLP-1 compound is liraglutide.

Embodiment 11: MIC-1 compound according to embodiment 1, wherein the GLP-1 compound is dulaglutide.

Embodiment 12: MIC-1 compound according to embodiment 1, wherein the GLP-1 compound is a exenatide.

Embodiment 13: MIC-1 compound according to any of the preceding embodiments, wherein the dosage of the MIC-1 compound is 5-1000 nmol/individual/injection.

Embodiment 14: MIC-1 compound according to any of the preceding embodiments, wherein the dosage of the GLP-1 compound is 0.3-5.0 mg/individual/injection.

Embodiment 15: MIC-1 compound according to embodiments 7 and 9, wherein the dosage of semaglutide is 0.3-5.0 mg/individual/injection.

Embodiment 16: MIC-1 compound according to embodiments 8 and 10, wherein the dosage of liraglutide is 1.2-3 mg/individual/injection.

Embodiment 17: MIC-1 compound according to any of the preceding embodiments, wherein the MIC-1 compound is administered simultaneously with the GLP-1 compound.

Embodiment 18: MIC-1 compound according to any of the preceding embodiments, wherein the MIC-1 compound is administered separately with the GLP-1 compound.

Embodiment 19: MIC-1 compound according to any of the preceding embodiments, wherein the MIC-1 compound is administered sequentially with the GLP-1 compound.

Embodiment 20: MIC-1 compound according to any of the preceding embodiments, wherein the MIC-1 compound and GLP-1 compound is administered subcutaneously.

Embodiment 21: MIC-1 compound according to embodiments 1-19, wherein the MIC-1 compound and GLP-1 compound is administered orally.

Embodiment 22: MIC-1 compound according to embodiments 1-19, wherein the MIC-1 compound or GLP-1 compound is administered orally.

Embodiment 23: MIC-1 compound according to embodiments 1-19, wherein the MIC-1 compound is administered subcutaneously and the GLP-1 compound is administered orally.

Embodiment 24: MIC-1 compound according to any of the preceding embodiments, wherein the MIC-1 compound is administered once daily, once weekly or once monthly.

Embodiment 25: MIC-1 compound according to any of the preceding embodiments, wherein the GLP-1 compound is administered once daily, once weekly or once monthly.

Embodiment 26: MIC-1 compound according embodiments 1-19, wherein the MIC-1 compound is administered subcutaneously once monthly.

Embodiment 27: MIC-1 compound according to embodiments 1-19 or 26, wherein the GLP-1 compound is administered subcutaneously once weekly.

Embodiment 28: MIC-1 compound according to embodiments 1-19 or 26, wherein the GLP-1 compound is administered orally once weekly.

Embodiment 29: Method of prevention and/or treatment of obesity, wherein a MIC-1 compound is administered simultaneously, separately or sequentially with a GLP-1 compound.

Embodiment 30: MIC-1 compound for use in the manufacture of a medicament for prevention and/or treatment of an eating disorder, such as obesity, wherein the MIC-1 compound is administered simultaneously, separately or sequentially with a GLP-1 compound.

Embodiment 31: A composition comprising a MIC-1 compound and a GLP-1 compound for use in the prevention and/or treatment of obesity.

EXAMPLES

Production of Compounds
MIC-1 Compounds
Production and purification of MIC-1-HSA compounds is described in WO2015197446 and may be prepared as described in Example 01 (Compound no. 7).
GLP-1 Compounds
Production and purification of liraglutide is described and may be prepared as described in WO98/08871, Example 37.
Production and purification of semaglutide is described and may be prepared as described in WO2006/097537, Example 4. Semaglutide is also known as N6.26-{18-[N-(17-carboxyheptadecanoyl)-L-γ-glutamyl]-10-oxo-3,6,12,15-tetraoxa-9,18-diazaoctadecanoyl}-[8-(2-amino-2-propanoic acid),34-L-arginine]human glucagon-like peptide 1(7-37), see WHO Drug Information Vol. 24, No. 1, 2010.

Example 1

Anti-Obesity Effects of HSA-MIC-1 In Combinations with Liraglutide

The purpose of the study in example 1 was to investigate effects of a MIC-1-HSA compound in combination with the GLP-1 compound liraglutide on body weight lowering in obese rat.
Formulations
MIC-1-HSA was dissolved in 140 mM sodium chloride, 1.96 mM potassium dihydrogen phosphate, 8.05 mM sodium phosphate dibasic, 500 ppm polysorbate at pH 7.4.
Liraglutide was formulated 14.0 mg/ml 1,2-propandiol, 1.42 mg/ml disodium phosphate, dihydrate, 5.5 mg/ml Phenol, pH: 8.15.
In Vivo Pharmacology Experiment
64 male obese Sprague Dawley rats from Taconic were used. Animals had ad libitum access to a high-fat diet (45 kcal % fat, Research Diets Inc, diet 12451). Mean starting body weight was 807.3 g (690.1-905.2 g) Animals were randomised into 8 groups based on body their weight (n=6-8). The rats were single-housed in reversed light cycle (dark 11:00-23:00) during the duration of the study. Vehicle and liraglutide were dosed subcutaneously (SC) once daily (QD) for the duration of the study (Day 0-26) at 10 am. Because of the immunogenic properties of MIC-1-HSA in rodents, the dosing period with MIC-1-HSA was limited to 12 days. MIC-1-HSA was dosed SC every other day, starting at study day 14 and ending at day 26. The two compounds were in all cases dosed individually and were not administrated in the same formulation using the same syringe. Table 1.

TABLE 1

Overview of dosing groups, number of replicates and doses.

| Group | N | Period 1 (Day 0 to 13) | Period 2 (Day 14 to 26) |
|---|---|---|---|
| 1 | 8 | Vehicle | Vehicle |
| 2 | 8 | Liraglutide 0.1 mg/kg | Liraglutide. 0.1 mg/kg |
| 3 | 8 | Vehicle | MIC-1-HSA. 0.44 nmol/kg |
| 4 | 8 | Liraglutide 0.1 mg/kg | Liraglutide. 0.1 mg/kg + MIC-1-HSA 0.44 nmol/kg |
| 5 | 8 | Vehicle | MIC-1-HSA. 2.2 nmol/kg |
| 6 | 8 | Liraglutide 0.1 mg/kg | Liraglutide 0.1 mg/kg + MIC-1-HSA. 2.2 nmol/kg |
| 7 | 8 | Vehicle | MIC-1-HSA. 11 nmol/kg |

TABLE 1-continued

Overview of dosing groups, number of replicates and doses.

| Group | N | Period 1 (Day 0 to 13) | Period 2 (Day 14 to 26) |
|---|---|---|---|
| 8 | 8 | Liraglutide 0.1 mg/kg | Liraglutide 0.1 mg/kg + MIC-1-HSA. 11 nmol/kg |

Dose Setting

Due to a long in vivo terminal half-life of MIC-1 HSA (~50 hrs in lean rat) animals were dosed with a bolus dose at day 14 and subsequent doses of MIC-1-HSA were reduced to compensate for the protracted half-life to achieve a stable plasma exposure during the study. A pharmacokinetic simulation estimated a ratio of 2.3 between the MIC-1 HSA bolus dose and maintenance doses to achieve this. MIC-1-HSA doses were set to (bolus/maintenance) 25/11 nmol/kg, 5.0/2.2 nmol/kg and 1.0/0.44 nmol/kg. Dose volume was adjusted to daily body weight. Table 1.

The dose of liraglutide was 0.1 mg/kg (27 nmol/kg) and was selected in order to achieve a therapeutic relevant pharmacodynamic effect. Table 1.

Body Weight

The body weight (BW) was monitored daily prior to dosing from day −1 to day 26.

Dosing

The dosing was performed using insulin syringe and a dosing volume of 1 ml/kg (2.3 ml/kg for bolus dose of MIC-1-HSA).

Results

In table 2 are shown pharmacodynamic effects expressed as changes in body weights of obese rats in response to the 8 treatment arms. Data are expressed as the average values as grams (A) and as percentages (B). "Delta 0-26" is the change in body weight from day 0 to day 26. "vs vehicle" is the change in body weight at day 26 in comparison with the vehicle group at day 26. "Predicted" is the expected change in body weight based on body weight changes in the associated MIC-1-HSA and liraglutide mono-therapy arms. "Synergy" expresses the unexpected and additional effect beyond the predicted effect of the MIC-1-HSA and liraglutide combination. This value is calculated by subtracting the predicted value from the actual effect of the combination (vs vehicle). A negative synergy value reflects an additional unexpected synergistic body weight lowering effect.

TABLE 2

Effect of treatments on body weight changes of obese rats

| A | Body weight [gram] | Study start | SD | Study end | SD | Delta 0-26 | vs vehicle | Predicted | Synergy |
|---|---|---|---|---|---|---|---|---|---|
| 1 | Vehicle | 807 | 63 | 798 | 71 | −9 | | | |
| 2 | Lira 100 μg/kg | 806 | 58 | 724 | 44 | −82 | −72 | | |
| 3 | Veh/MIC-1 HSA 0.44 nmol/kg | 805 | 56 | 738 | 55 | −68 | −58 | | |
| 4 | Lira + MIC-1 HSA 0.44 nmol/kg | 806 | 56 | 652 | 39 | −153 | −144 | −131 | −13 |
| 5 | Veh/MIC-1 HSA 2.2 nmol/kg | 807 | 54 | 737 | 57 | −71 | −61 | | |
| 6 | Lira + MIC-1 HSA 2.2 nmol/kg | 811 | 56 | 609 | 41 | −202 | −193 | −134 | −59 |
| 7 | Veh/MIC-1 HSA 11 nmol/kg | 806 | 49 | 723 | 44 | −84 | −74 | | |
| 8 | Lira + MIC-1 HSA 11 nmol/kg | 811 | 50 | 619 | 48 | −192 | −183 | −147 | −36 |

| B | Body weight [% of study start] | Study start | SD | Study end | SD | Delta 0-26 | vs vehicle | | Synergy |
|---|---|---|---|---|---|---|---|---|---|
| 1 | Vehicle | 100 | N/A | 99 | 2.1 | −1.2 | | | |
| 2 | Lira 100 μg/kg | 100 | N/A | 90 | 2.2 | −10.0 | −8.8 | | |
| 3 | Veh/MIC-1 HSA 0.44 nmol/kg | 100 | N/A | 92 | 2.2 | −7.8 | −6.6 | | |
| 4 | Lira + MIC-1 HSA 0.44 nmol/kg | 100 | N/A | 81 | 2.2 | −19.0 | −17.8 | −15.5 | −2.3 |
| 5 | Veh/MIC-1 HSA 2.2 nmol/kg | 100 | N/A | 91 | 1.6 | −8.8 | −7.6 | | |
| 6 | Lira + MIC-1 HSA 2.2 nmol/kg | 100 | N/A | 75 | 2.1 | −24.9 | −23.6 | −16.4 | −7.2 |
| 7 | Veh/MIC-1 HSA 11 nmol/kg | 100 | N/A | 90 | 1.9 | −10.4 | −9.1 | | |
| 8 | Lira + MIC-1 HSA 11 nmol/kg | 100 | N/A | 76 | 4.6 | −23.6 | −22.4 | −18.0 | −4.4 |

Liraglutide as monotherapy reduced body weight by 8.8% as compared to vehicle. Table 2B.

MIC-1-HSA as monotherapy reduced body weight by 6.6% in the 0.44 nmol/kg group, by 7.6% in the 2.2 nmol/kg dose group and by 9.1% in the 11 nmol/kg group compared to vehicle. Table 2B.

Combination therapy of MIC-1-HSA with liraglutide reduced body weights by 17.8%, by 23.6% and by 22.4% in combination with the low dose, medium dose and high dose of MIC-1-HSA, respectively, compared to vehicle. Table 2B.

In numerical terms, the combinations of liraglutide and MIC-1-HSA-1 were in all cases more effective in reducing body weight (table 2B, synergy) than predicted by the additive effects of the respective mono-therapy arms (Table 2B, predicted).

Based on an ordinary 2 way ANOVA analysis of the 3 combinations and respective mono-therapies (percent change at day 26 compared with day 0, Graphpad Prism 7.0), the effect of both MIC-1-HSA and liraglutide was highly significant (p<0.0001) and there was also an significant interaction (p=0.0016) between treatments meaning that the combinations were significantly more efficacious on body weight lowering than would be expected based by the effects of the respective MIC-1-HSA and liraglutide mono-therapy arms. Thus, combining MIC-1-HSA and liraglutide in obese male rat results in an unexpected synergistically effect on body weight lowering.

Example 2

Anti-Obesity Effects of HSA-MIC-1 In Combinations with Semaglutide

The purpose of the study in example 2 was to investigate effects of a MIC-1-HSA compound in combination with the GLP-1 compound semaglutide on body weight lowering in obese rat.

Formulations

MIC-1-HSA was dissolved in 140 mM sodium chloride, 1.96 mM potassium dihydrogen phosphate, 8.05 mM sodium phosphate dibasic, 500 ppm polysorbate at pH 7.4.

Semaglutide was dissolved in 50 mM phosphate, 70 mM sodium chloride, 0.05% polysorbate 80 at pH 7.4.

In Vivo Pharmacology Experiment 60 male obese Sprague Dawley rats from Taconic were used. Animals where housed 2 per cage and had ad libitum access to high-fat diet (45 kcal % fat, Research Diets Inc, diet 12451). Mean starting body weight was 736.0 g (634.7-982.4 g). Animals were randomised into 6 groups based on body weight (n=10). Animals were housed in reversed light cycle (dark 11:00-23:00). Vehicle and semaglutide were dosed subcutaneously (SC) once daily (QD) for the duration of the study (study day 0-26) at 10 am. Because of the immunogenic properties of MIC-1-HSA in rodents, the dosing period with MIC-1-HSA was limited to 12 days. MIC-1-HSA was dosed SC every other day, starting at study day 15 and ending at day 26. The two compounds were in all cases dosed individually and were not administrated in the same formulation using the same syringe. Table 3.

TABLE 3

Overview of dosing groups, number of replicates and doses

| Group | N | Periode 1 (Day 1 to 14) | Periode 2 (Day 15 to 26) |
|---|---|---|---|
| 1 | 10 | Vehicle | Vehicle |
| 2 | 10 | Semaglutide 2 nmol/kg | Semaglutide 2 nmol/kg |
| 3 | 10 | Vehicle | MIC-1-HSA. 0.44 nmol/kg |
| 4 | 10 | Semaglutide 2 nmol/kg | Semaglutide 2 nmol/kg + MIC-1-HSA. 0.44 nmol/kg |
| 5 | 10 | Vehicle | MIC-1-HSA. 11 nmol/kg |
| 6 | 10 | Semaglutide 2 nmol/kg | Semaglutide 2 nmol/kg + MIC-1-HSA. 11 nmol/kg |

Dose Setting

Due to a long in vivo terminal half-life of MIC-1 HSA (~50 hrs in lean rat) animals were dosed with a bolus dose at day 15 and subsequent doses of MIC-1-HSA were reduced to compensate for the protracted half-life to achieve a stable plasma exposure during the study. A pharmacokinetic simulation estimated a ratio of 2.3 between the MIC-1 HSA bolus dose and maintenance doses to achieve this. A pharmacokinetic simulation suggested a ratio of 2.3 between the MIC-1 HSA bolus dose and maintenance doses to achieve this. MIC-1-HSA doses were set to (bolus/maintenance) 25/11 nmol/kg and 1.0/0.44 nmol/kg. Dose volume was adjusted to daily body weight. Please see table 3.

The dose of Semaglutide was 2 nmol/kg and was selected in order to achieve a therapeutic relevant pharmaco-dynamic effect. Table 3.

Body Weight

From day −1 and during the entire dosing period until day 26, body weight was monitored daily prior to dosing.

Dosing

The dosing was performed using insulin syringe and a dosing volume of 1 ml/kg (2.3 ml/kg for bolus dose of MIC-1-HSA).

Results

In table 4 are shown pharmacodynamic effects expressed as changes in body weights of obese rats in response to the 6 treatment arms. Data are expressed as the average values as grams (A) and as percentages (B). "Delta 0-26" is the change in body weight from day 0 to day 26. "vs vehicle" is the change in body weight at day 26 in comparison with the vehicle group at day 26. "Predicted" is the expected change in body weight based on body weight changes in the associated MIC-1-HSA and semaglutide mono-therapy arms. "Synergy" expresses the unexpected and additional effect beyond the predicted effect of the MIC-1-HSA and semaglutide combination. This value is calculated by subtracting the predicted value from the actual effect of the combination (vs vehicle). A negative synergy value reflects an additional unexpected synergistic body weight lowering effect.

TABLE 4

Effect of treatments on body weight changes of obese rats

| A | Body weight [gram] | Study start | SD | Study end | SD | Delta 0-26 | vs vehicle | Predicted | Synergy |
|---|---|---|---|---|---|---|---|---|---|
| 1 | Vehicle | 777 | 63 | 797 | 74 | 20.4 | | | |
| 2 | Sema 2 nmol/kg | 788 | 107 | 746 | 109 | −41.8 | −62.2 | | |
| 3 | Veh/MIC-1 HSA 0.44 nmol/kg | 736 | 77 | 714 | 72 | −21.3 | −41.7 | | |
| 4 | Sema + MIC-1 HSA 0.44 nmol/kg | 740 | 69 | 667 | 59 | −72.5 | −92.9 | −103.9 | 11.0 |
| 5 | Veh/MIC-1 HSA 11 nmol/kg | 769 | 76 | 711 | 72 | −58.3 | −78.6 | | |

TABLE 4-continued

Effect of treatments on body weight changes of obese rats

| | | | | | | | | | |
|---|---|---|---|---|---|---|---|---|---|
| 6 | Sema + MIC-1 HSA 11 nmol/kg | 717 | 54 | 570 | 53 | −146.7 | −167.1 | −140.8 | −26.2 |

| B | Body weight [% of study start] | Study start | SD | Study end | SD | Delta 0-26 | vs vehicle | Predicted | Synergy |
|---|---|---|---|---|---|---|---|---|---|
| 1 | Vehicle | 100 | N/A | 103 | 2.9 | 2.6 | | | |
| 2 | Sema 2 nmol/kg | 100 | N/A | 95 | 1.7 | −5.4 | −8.0 | | |
| 3 | Veh/MIC-1 HSA | 100 | N/A | 97 | 2.7 | −2.8 | −5.4 | | |
| 4 | Sema + MIC-1 HSA | 100 | N/A | 89 | 2.6 | −10.8 | −13.3 | −13.4 | 0.1 |
| 5 | Veh/MIC-1 HSA MD | 100 | N/A | 91 | 3.1 | −8.7 | −11.3 | | |
| 6 | Sema + MIC-1 HSA | 100 | N/A | 79 | 2.5 | −20.5 | −23.1 | −19.3 | −3.8 |

Semaglutide as monotherapy reduced body weight by 8.0% as compared to vehicle.

MIC-1-HSA as monotherapy reduced body weight by 5.4% in the 0.44 nmol/kg group and 11.3% in the in the 11 nmol/kg group compared to vehicle. Table 4B.

Combination therapy of MIC-1-HSA with semaglutide reduced body weights by 13.3% and by 23.1% in combination with the 0.44 nmol/kg and 11 nmol/kg of MIC-1-HSA, respectively, compared to vehicle. Table 4B.

In numerical terms, the combinations of semaglutide and MIC-1-HSA-1 was in the high dose group more effective in reducing body weight (table 4B, synergy) than predicted by the additive effect of the respective mono therapy arms (table 4B, predicted column).

Based on an ordinary 2 way ANOVA analysis of the 2 combinations and respective mono-therapies (percent changes at day 26 compared with day 0, Graphpad Prism 7.0), the effect of both MIC-1-HSA and semaglutide was highly significant (p<0.0001) and there was also a significant interaction (p=0.0374) between treatments meaning that the combinations were significantly more efficacious on body weight lowering than would be expected based by the effects of the respective MIC-1-HSA and semaglutide monotherapy arms. Thus, combining MIC-1-HSA and semaglutide in obese male rat results in a unexpected synergistically effect on body weight lowering.

While certain features of the invention have been illustrated and described herein, many modifications, substitutions, changes, and equivalents will now occur to those of ordinary skill in the art. It is, therefore, to be understood that the appended embodiments are intended to cover all such modifications and changes as fall within the true spirit of the invention.

The invention claimed is:

1. A method for treating obesity, comprising administering a MIC-1 compound and a GLP-1 compound to a subject in need thereof, wherein the MIC-1 compound is a MIC-1 fused with human serum albumin; wherein the GLP-1 compound is selected from the group consisting of liraglutide and semaglutide; and wherein the MIC-1 compound is administered simultaneously, separately, or sequentially with the GLP-1 compound.

2. The method according to claim 1, wherein the dosage of the MIC-1 compound is 5-1000 nmol/individual/injection.

3. The method according to claim 1, wherein the dosage of the GLP-1 compound is 0.3-5.0 mg/individual/injection.

4. The method according to claim 1, wherein the MIC-1 compound and GLP-1 compound are administered subcutaneously or orally.

5. The method according to claim 1, wherein the MIC-1 compound is administered once daily, once weekly, or once monthly.

6. The method according to claim 1, wherein the GLP-1 compound is administered once daily, once weekly, or once monthly.

7. The method according to claim 1, wherein the GLP-1 compound is liraglutide.

8. The method according to claim 7, wherein the dosage of the MIC-1 compound is 5-1000 nmol/individual/injection.

9. The method according to claim 7, wherein the dosage of the GLP-1 compound is 0.3-5.0 mg/individual/injection.

10. The method according to claim 7, wherein the MIC-1 compound and GLP-1 compound are administered subcutaneously or orally.

11. The method according to claim 7, wherein the MIC-1 compound is administered once daily, once weekly, or once monthly.

12. The method according to claim 7, wherein the GLP-1 compound is administered once daily, once weekly, or once monthly.

13. The method according to claim 1, wherein the GLP-1 compound is semaglutide.

14. The method according to claim 13, wherein the dosage of the MIC-1 compound is 5-1000 nmol/individual/injection.

15. The method according to claim 13, wherein the dosage of the GLP-1 compound is 0.3-5.0 mg/individual/injection.

16. The method according to claim 13, wherein the MIC-1 compound and GLP-1 compound are administered subcutaneously or orally.

17. The method according to claim 13, wherein the MIC-1 compound is administered once daily, once weekly, or once monthly.

18. The method according to claim 13, wherein the GLP-1 compound is administered once daily, once weekly, or once monthly.

* * * * *